US 10,863,925 B2

(12) United States Patent
Takatsuka et al.

(10) Patent No.: US 10,863,925 B2
(45) Date of Patent: Dec. 15, 2020

(54) INFORMATION PROCESSING DEVICE

(71) Applicant: SONY CORPORATION, Tokyo (JP)

(72) Inventors: Susumu Takatsuka, Tokyo (JP);
Yutaka Murakami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/339,957

(22) PCT Filed: Sep. 14, 2017

(86) PCT No.: PCT/JP2017/033288
§ 371 (c)(1),
(2) Date: Apr. 5, 2019

(87) PCT Pub. No.: WO2018/092398
PCT Pub. Date: May 24, 2018

(65) Prior Publication Data

US 2019/0282129 A1    Sep. 19, 2019

(30) Foreign Application Priority Data

Nov. 15, 2016   (JP) .................................. 2016-222295

(51) Int. Cl.
*A61B 5/11*      (2006.01)
*A61B 5/00*      (2006.01)
(Continued)

(52) U.S. Cl.
CPC ............ *A61B 5/1116* (2013.01); *A61B 5/107* (2013.01); *A61B 5/1118* (2013.01); *A61B 5/486* (2013.01);
(Continued)

(58) Field of Classification Search
CPC ..... A61B 5/1118; A61B 5/107; A61B 5/1116; A61B 5/486; A61B 5/7405; A61B 5/742;
(Continued)

(56) References Cited

U.S. PATENT DOCUMENTS 9,826,299 B1 *   11/2017   Osterhout ............. G06F 1/1686
2015/0100251 A1 *   4/2015   Solinsky ............. G01L 19/0092
702/33

(Continued)

FOREIGN PATENT DOCUMENTS

EP         2018825 A1       1/2009
JP       2004-041387 A      2/2004
(Continued)

OTHER PUBLICATIONS

International Search Report and Written Opinion of PCT Application No. PCT/JP2017/033288, dated Nov. 14, 2017, 11 pages of ISRWO.

(Continued)

*Primary Examiner* — Daniel Previl
(74) *Attorney, Agent, or Firm* — Chip Law Group

(57) ABSTRACT

Provided is an information processing device that includes a determination portion that determines, on the basis of information regarding an exercise state of a user, whether the exercise state of the user is a sitting state or a standing state, and a display processing portion that performs processing for displaying at least one of a time when the exercise state of the user changes from the sitting state to the standing state or the number of times the exercise state of the user changes from the sitting state to the standing state.

6 Claims, 9 Drawing Sheets

(51) Int. Cl.
  *G08B 21/18* (2006.01)
  *A61B 5/107* (2006.01)
(52) U.S. Cl.
  CPC ............ *A61B 5/742* (2013.01); *A61B 5/7405*
       (2013.01); *G08B 21/18* (2013.01)
(58) Field of Classification Search
  CPC ... A61B 2503/10; A61B 5/0205; A61B 5/024;
        A61B 5/1125; A61B 5/6898; A61B
        5/7275; G08B 21/18; A63B 24/0006;
        A63B 24/0062; G06F 1/3231; G06F
        1/3234; G06F 3/017; G06F 3/0346; G06F
        3/0416; G06F 3/0488; G06Q 30/02;
        G06Q 30/0207; G06Q 50/22; G16H
        20/30; H04M 19/04; H04M 19/047;
        H04M 1/72569; H04M 2250/12
  USPC ....... 340/573.7, 575, 691.6, 692, 686.1, 3.1,
                                340/7.55, 7.57, 286.07
  See application file for complete search history.

(56) References Cited

U.S. PATENT DOCUMENTS

| | | | | |
|---|---|---|---|---|
| 2016/0174903 | A1* | 6/2016 | Cutaia | A61B 5/0816 600/301 |
| 2017/0017776 | A1* | 1/2017 | Soulos | G06F 19/3475 |
| 2017/0065187 | A1* | 3/2017 | Hsieh | A61B 5/6823 |
| 2018/0035973 | A1* | 2/2018 | Shusterman | A61B 5/02116 |
| 2019/0254590 | A1* | 8/2019 | Venkatraman | A61B 5/0205 |

FOREIGN PATENT DOCUMENTS

| | | |
|---|---|---|
| JP | 2006-180899 A | 7/2006 |
| JP | 2008-167783 A | 7/2008 |
| JP | 2010-017525 A | 1/2010 |
| WO | 2016/051379 A1 | 4/2016 |
| WO | 2016/106299 A1 | 6/2016 |

OTHER PUBLICATIONS

Garcia-Garcia, et al., "Statistical Machine Learning for Automatic Assessment of Physical Activity Intensity Using Multi-Axial Accelerometry and Heart Rate", 10 pages.
Mya Nelson "New Research: Getting Up From Your Desk Can Put the "Breaks" on Cancer", 2017 American Institute for Cancer Research, Nov. 3, 2011, pp. 1-5.
García-García, et al., "Statistical Machine Learning for Automatic Assessment of Physical Activity Intensity Using Multi-axial Accelerometry and Heart Rate", Conference on Artificial Intelligence in Medicine in Europe, AIME 2011: Artificial Intelligence in Medicine, 2011, pp. 70-79.
Mya Nelson, "New Research: Getting Up From Your Desk Can Put the "Breaks" on Cancer", The American Institute for Cancer Research, Nov. 3, 2011, 5 pages.
Mya Nelson, "New Research: Getting Up From Your Desk Can Put the "Breaks" on Cancer", 2017 American Institute for Cancer Research, Meet AICR’, 05 pages.

* cited by examiner

INFORMATION PROCESSING DEVICE

CROSS REFERENCE TO RELATED APPLICATIONS

This application is a U.S. National Phase of International Patent Application No. PCT/JP2017/033288 filed on Sep. 14, 2017, which claims priority benefit of Japanese Patent Application No. JP 2016-222295 filed in the Japan Patent Office on Nov. 15, 2016. Each of the above-referenced applications is hereby incorporated herein by reference in its entirety.

TECHNICAL FIELD

The present disclosure relates to an information processing device and a program.

BACKGROUND ART

Hitherto, for example, Patent literature 1 below describes a technique intended to instruct a user to perform proper exercise for a proper time by allowing the user to easily grasp the current pulse condition. Further, Non-patent literature 1 below describes a relationship between a sitting activity time and a health risk.

CITATION LIST

Patent Literature

Patent Literature 1: JP 2008-167783A

Non-Patent Literature

Non-Patent Literature 1: Mya Nelson, "New Research: Getting Up From Your Desk Can Put the "Breaks" on Cancer", Nov. 3, 2011, American Institute for Cancer Research (AICR), [Search conducted on Nov. 11, 2016], Internet <URL: http://www.aicr.org/press/press-releases/getting-up-from-your-desk.html>.

DISCLOSURE OF INVENTION

Technical Problem

A human usually repeats states of sitting, standing, exercising, and the like throughout the day. In accordance with recent studies, it is known that a person's health condition is deteriorated as the time of the sitting state becomes longer. For example, if the person who takes sufficient exercise continues to sit on the chair in a non-exercise time, the person's health condition is deteriorated due to the prolonged time of the sitting state.

Although the technique described in Patent literature) above is intended to instruct the user to perform proper exercise on the basis of the pulse condition, no consideration is given to as to whether the health condition caused by the prolonged time of the sitting state is improved.

Thus, it is desired to maintain the good health condition by preventing the prolonged sitting time.

Solution to Problem

According to the present disclosure, there is provided an information processing device including: a determination portion that determines, on the basis of information regarding an exercise state of a user, whether the exercise state of the user is a sitting state or a standing state; and a display processing portion that performs processing for displaying at least one of a time when the exercise state of the user changes from the sitting state to the standing state or the number of times the exercise state of the user changes from the sitting state to the standing state.

In addition, according to the present disclosure, there is provided a program for causing a computer to function as: a means of determining, on the basis of information regarding an exercise state of a user, whether the exercise state of the user is a sitting state or a standing state; and a means of performing processing for displaying at least one of a time when the exercise state of the user changes from the sitting state to the standing state or the number of times the exercise state of the user changes from the sitting state to the standing state.

Advantageous Effects of Invention

According to the present disclosure, it becomes possible to maintain the good health condition by preventing the prolonged sitting time.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
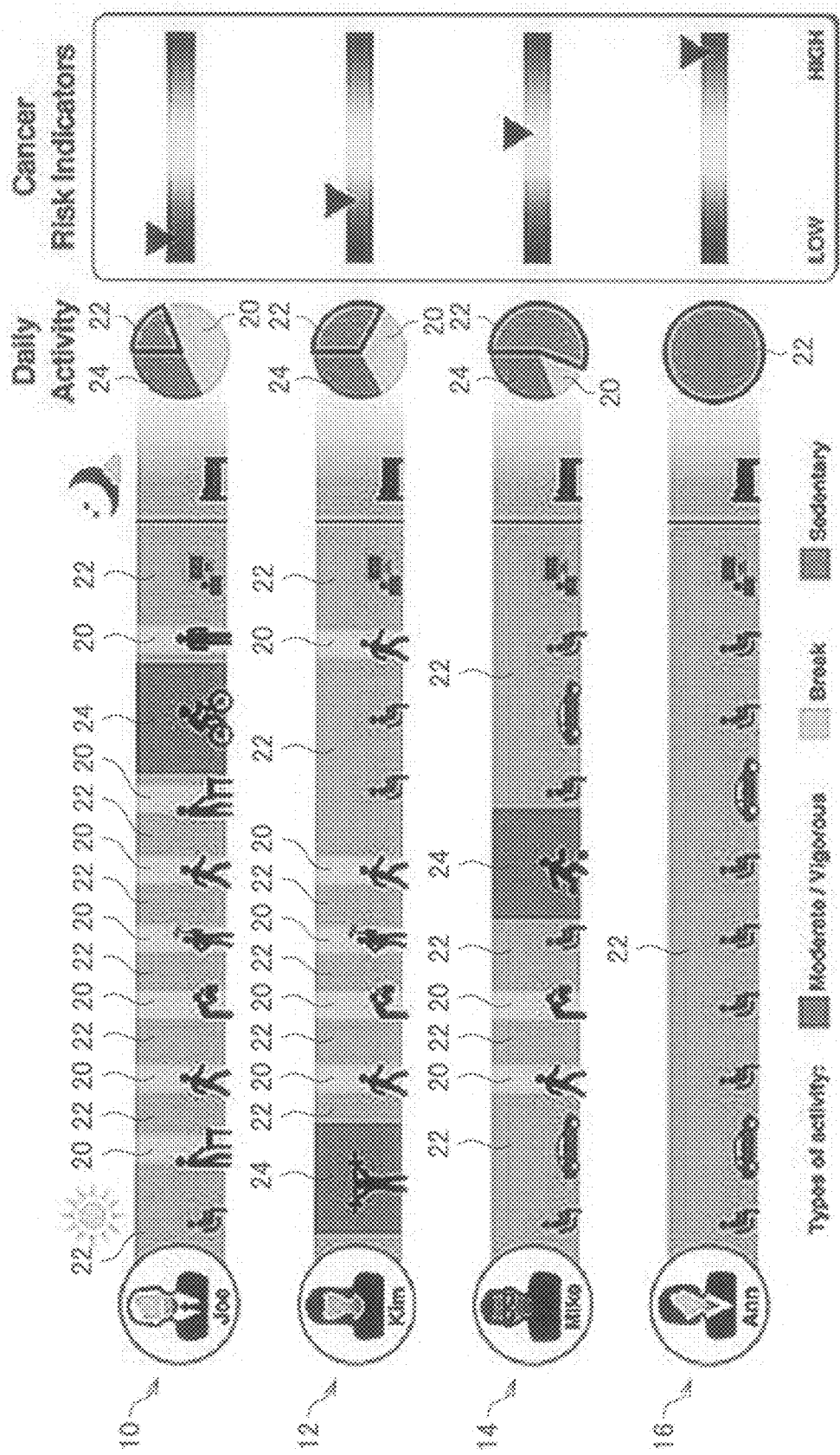
FIG. 1 is a schematic diagram illustrating a relationship between a sitting activity time and a health risk.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. Background
2. Configuration example of device according to present embodiment
3. Determination of user activity
4. Display example of touch panel display and processing for performing display
5. Cooperation with other devices such as smartphone and server 1. Background Person's states in a daily life normally include a sitting state where the person sits on the chair, a standing state where the person is on his/her feet, a state where the person is carrying out moderate exercise, a state where the person is carrying out vigorous exercise, and the like. It is known that such person's states in a daily life are related to the person's health. For example, FIG. 1 shows a schematic diagram illustrating a relationship between a sitting activity time and a health risk described in Non-patent literature 1 by American Institute for Cancer Research (AICR). In FIG. 1, the daily states of each of four subjects 10, 12, 14, and 16 are classified into a standing state (Break) 20, a sitting state (Sedentary) 22, and an exercise state (Moderate/Vigorous) 24 and associated with a cancer risk (Cancer Risk Indicators). As shown in FIG. 1, it is found that the cancer risk decreases as the time of the sitting state 22 is shorter. Further, although the total time of the exercise state 24 per day is almost the same in the subjects 10, 12, and 14, the cancer risk increases as the time of the sitting state 22 is longer. Thus, even if the moderate exercise is performed, the prolonged time of the sitting state 22 increases the cancer risk, indicating that the exercise alone cannot reduce the cancer risk. In particular, it is found that the cancer risk can be reduced by frequently breaking up the time of the sitting state 22 with the standing state 20 as observed in the subject 10.

From the aforementioned viewpoints, in the present embodiment, as described in detail below, information regarding the sitting state 22 is presented to the user through a user interface to warn the user not to continue the sitting state 22 for a long period of time and thereby maintain the health condition of the user.

2. Configuration Example of Device According to Present Embodiment

Figure 2:
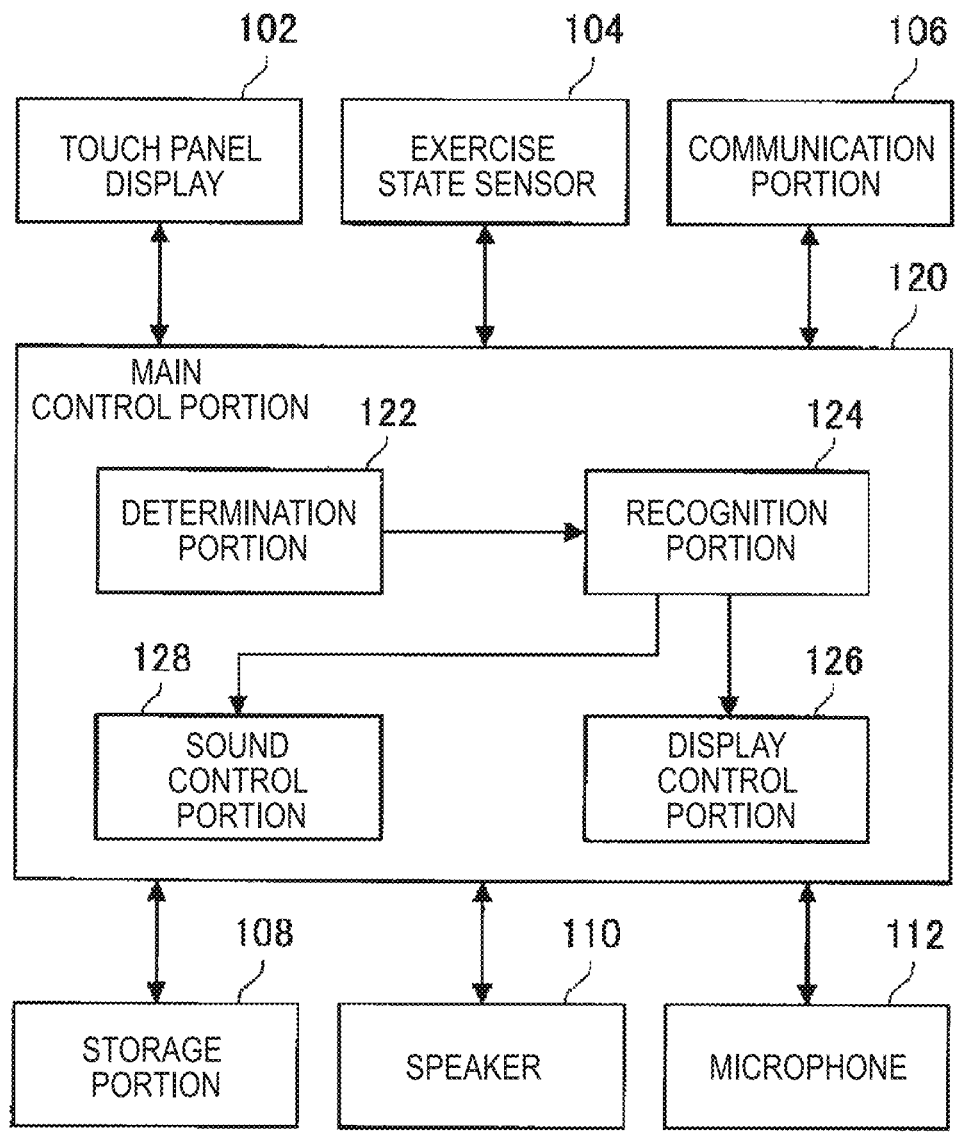
FIG. 2 is a schematic diagram illustrating a configuration of a device according to the present embodiment.

FIG. 2 is a schematic diagram illustrating a configuration of a device 100 according to the present embodiment. The device 100, which is a smartphone, a wearable device, or the like, is put on the body of the user. As shown in FIG. 2, the device 100 according to the present embodiment is configured by including a touch panel display 102, an exercise state sensor 104, a communication portion 106, a storage portion 108, a speaker 110, and a microphone 112. A control portion 120 is configured by including a determination portion 122, a recognition portion 124, a display control portion (a display processing portion) 126, and a sound control portion (a sound processing portion) 128. Note that each constituting element of the device 100 shown in FIG. 2 can be constitute by a hardware, or a central processing unit such as CPU and a program for causing the central processing unit to perform the function. Note that the device 100 may be free from the touch panel display 102, the communication portion 106, the speaker 110, and the microphone 112.

The exercise state sensor 104 includes a heart rate sensor and an acceleration sensor. The determination portion 122 of the control portion 120 determines, from a detection value of the exercise state sensor 104, whether the user is in the sitting state, the standing state, the state of carrying out the moderate exercise, the state of carrying out the vigorous exercise, or the like. The determination portion 120 can also determine the time when the user state changes from the sitting state to the standing state and the number of times the user state changes from the sitting state to the standing state within a predetermined time (e.g., per day). The recognition portion 124 recognizes whether or not the user state is the sitting state and also recognizes a continuous sitting time on the basis of a determination result of the determination portion 122. The display control portion 126 performs processing for displaying processing results of the determination portion 122 and the recognition portion 124 on the touch panel display 102. The sound control portion 128 performs processing for outputting via sound the processing results of the determination portion 122 and the recognition portion 124 from the speaker 110. Note that exercise state sensor 104 may include a sensor that detects other biological information such as a body temperature sensor and the determination portion 124 may determine the exercise state using multiple pieces of biological information such as the heartbeat and the body temperature.

3. Determination of User Activity

Figure 3:
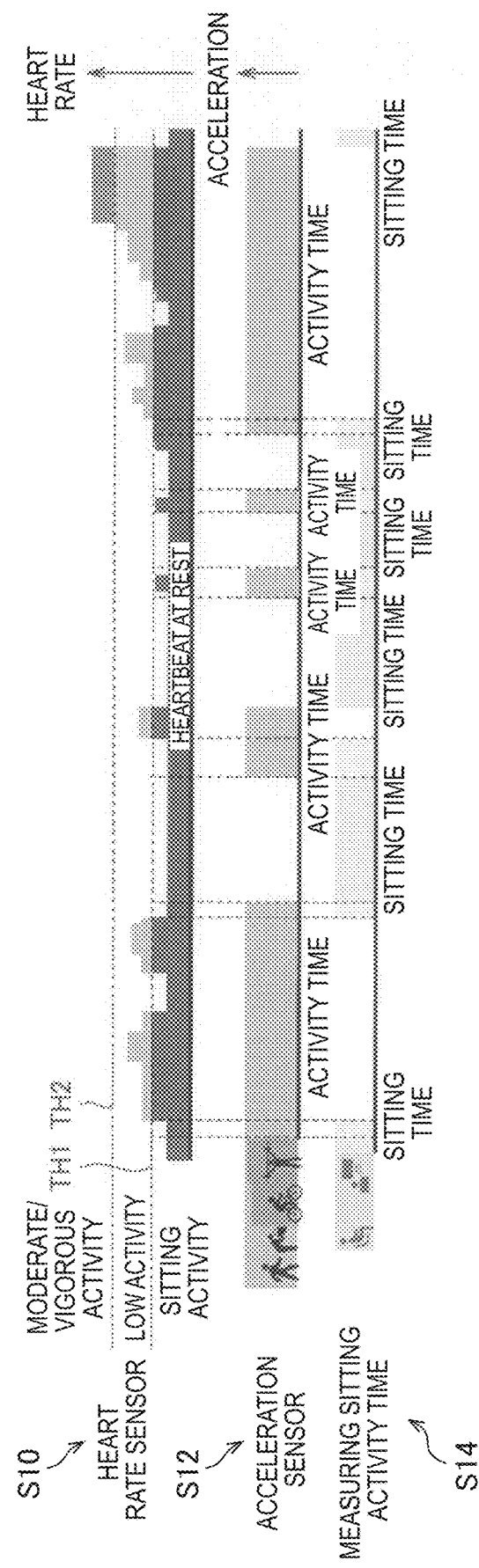
FIG. 3 is a schematic diagram describing how a determination portion determines an activity of a user.

FIG. 3 is a schematic diagram describing how the determination portion 122 determines the user activity. First, in a step S10, an activity amount of the user is determined from a heart rate at rest and a heart rate during activity. In this step, the activity amount is determined such that the heart rate of less than a threshold value TH1 indicates the sitting activity, the heart rate of the threshold value TH1 or more and less than the threshold value TH2 indicates a low activity (standing state), and the heart rate of more than the threshold value TH2 indicates a moderate activity and a vigorous activity (moderate and vigorous exercise).

Next, in a step S12, it is determined whether or not the user is in an active state from a detection value of the acceleration sensor. In this step, it is determined that the user is in the active state if an acceleration is a predetermined threshold value or more. Then, in a step S14, the time of the sitting activity is automatically measured on the basis of the determinations in the step S10 and the step S12. In this manner, distinction between the sitting state, the standing state, and the active state is made in accordance with the determination result by the heart rate sensor as well as the determination result of the activity amount by the acceleration sensor. Note that, as an example, the standing state refers to a state where a motion amount of the user is the motion amount equivalent to walking or less and more than the motion amount equivalent to sitting. Further, the active state refers to a state where the motion amount of the user is more than the motion amount equivalent to walking, such as a state of carrying out moderate exercise, vigorous exercise, or the like.

4. Display Example of Touch Panel Display and Processing for Performing Display

Figure 4:
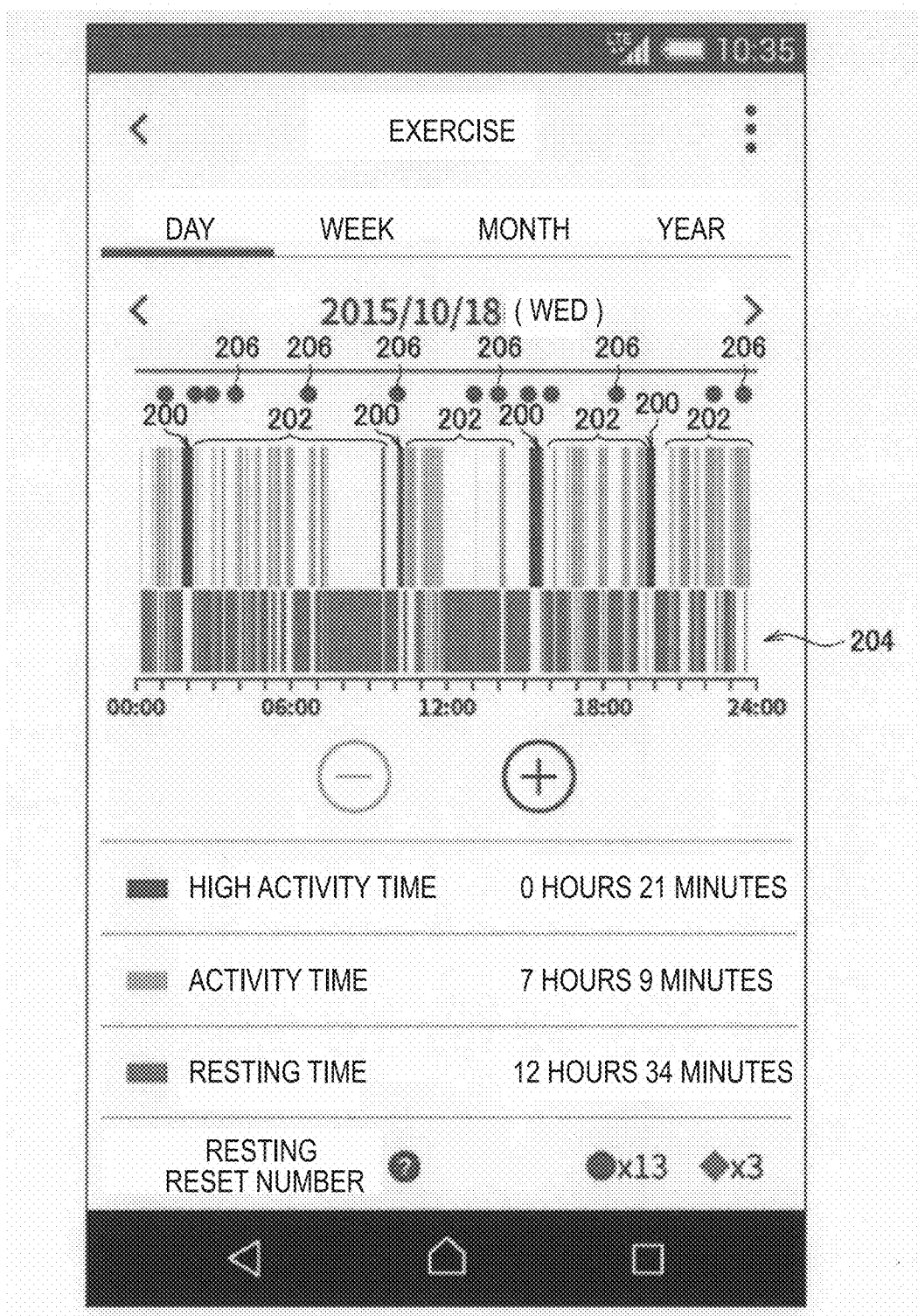
FIG. 4 is a schematic diagram illustrating a display example of a touch panel display of the device.

FIG. 4 is a schematic diagram illustrating a display example of the touch panel display 102 of the device 100. The touch panel display 102 displays a display 200 indicating an active time zone in which the user performs a relatively vigorous activity such as exercise, a display 202 indicating a standing time zone, and a display 204 indicating a sitting time zone regarding a daily activity of the user. Here, the display 202 indicating the standing time zone indicates that the user performed exercise lighter than walking (standing work or the like). The display 200 indicating the active time zone is displayed more densely than the display 202 indicating the standing time zone to be distinguished from the display 202 indicating the standing time zone. Note that the display example shown in FIG. 4 is just an example, and other display formats allowing the display of similar function may be used.

Further, the touch panel display 102 displays a display 206 indicating the time when the sitting state changes to the standing state. Hereinafter, processing for displaying the display 206 will be described.

Figure 5:
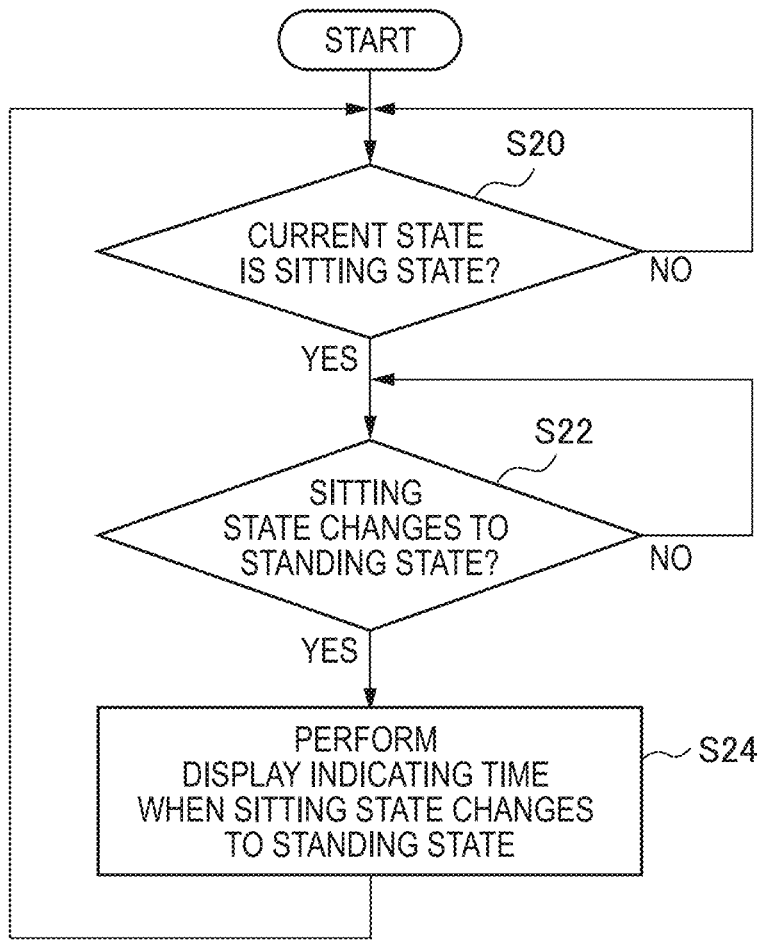
FIG. 5 is a flowchart describing processing for displaying a display indicating a time when a sitting state changes to a standing state.

FIG. 5 is a flowchart describing the processing for displaying the display 206 indicating the time when the sitting state changes to the standing state. First, in a step S20, it is determined whether or not the current state is the sitting state and, if the current state is the sitting state, the flow proceeds to a step S22. On the other hand, if the current state is not the sitting state, the flow waits at the step S20. In the step S22, it is determined whether or not the sitting state changes to the standing state and, if the sitting state changes to the standing state, the flow proceeds to a step S24. In the step S24, the display 206 indicating the time when the sitting state changes to the standing state is displayed. After the step S24, the flow returns to the step S20. On the other hand, if the sitting state does not change to the standing state in the step S22, the flow waits at the step S22. Note that, as described above, whether or not the current state is the sitting state is determined by the determination portion 122 of the control portion 120.

When the display 206 indicating the time when the sitting state changes to the standing state is displayed as shown in FIG. 4 in a manner described above, the user can confirm a frequency of the changes from the sitting state to the standing state by visually recognizing the display 206. This allows the user to recognize that the low frequency of the changes from the sitting state to the standing state affects the user's health, thereby motivating the user to change the sitting state to the standing state. As a result, the user can avoid the health risk.

Figure 6:
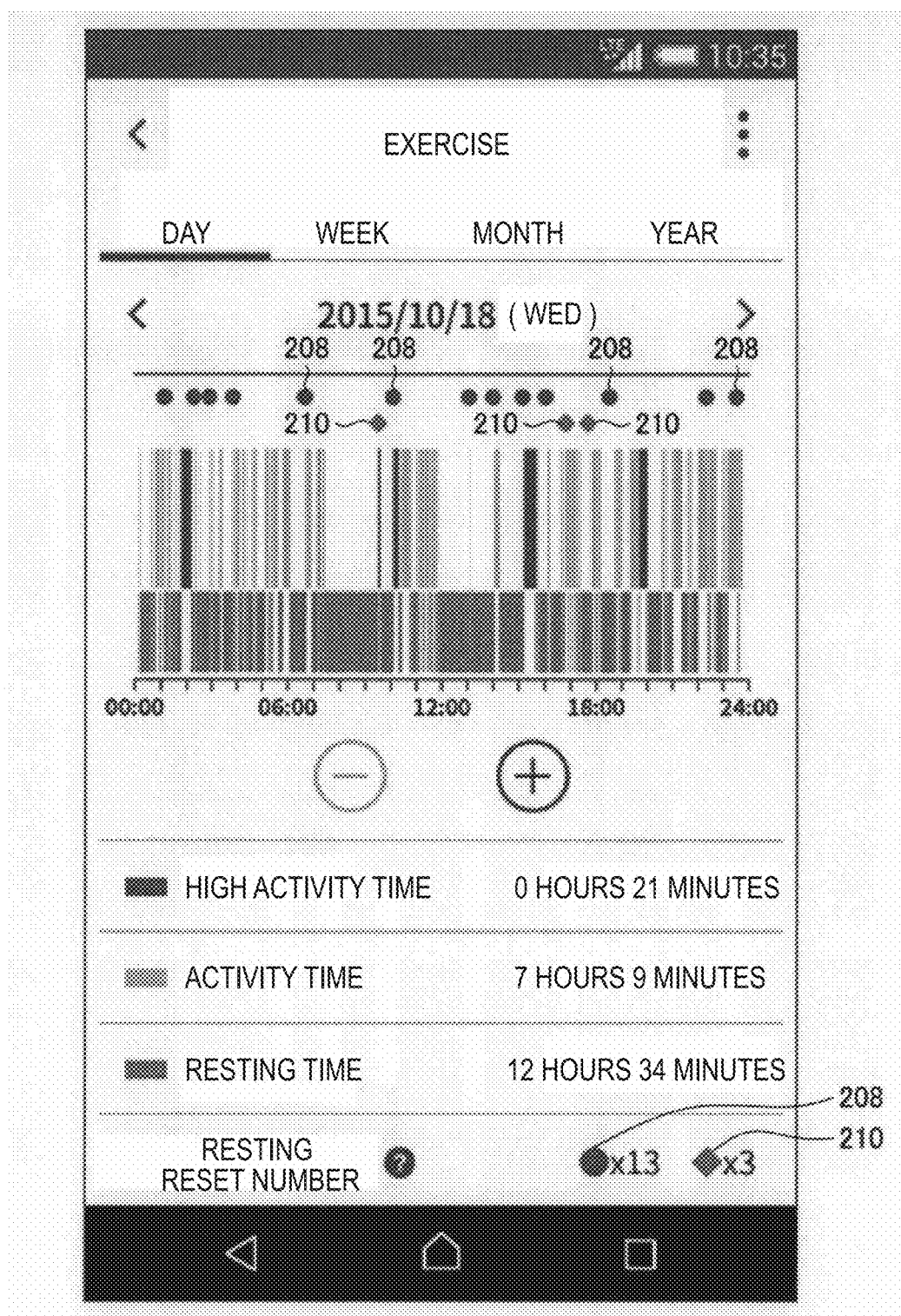
FIG. 6 is a schematic diagram illustrating an example in which a display indicating that a continuous sitting time is less than X minutes and a display indicating that a continuous sitting time is less than Y minutes are displayed on the touch panel display.

FIG. 6 shows an example in which the touch panel display 102 displays a display 208 indicating that the continuous sitting time is less than X minutes and a display 210 indicating that the continuous sitting time is less than Y minutes instead of the display 206 shown in FIG. 4. Further, as shown in FIG. 6, the number of the displays 208 (=13) and the number of the displays 210 (=3) are displayed at the lower right of the touch panel display 102. Note that the displays 200, 202, 204, and 206 are displayed similarly to FIG. 4.

Figure 7:
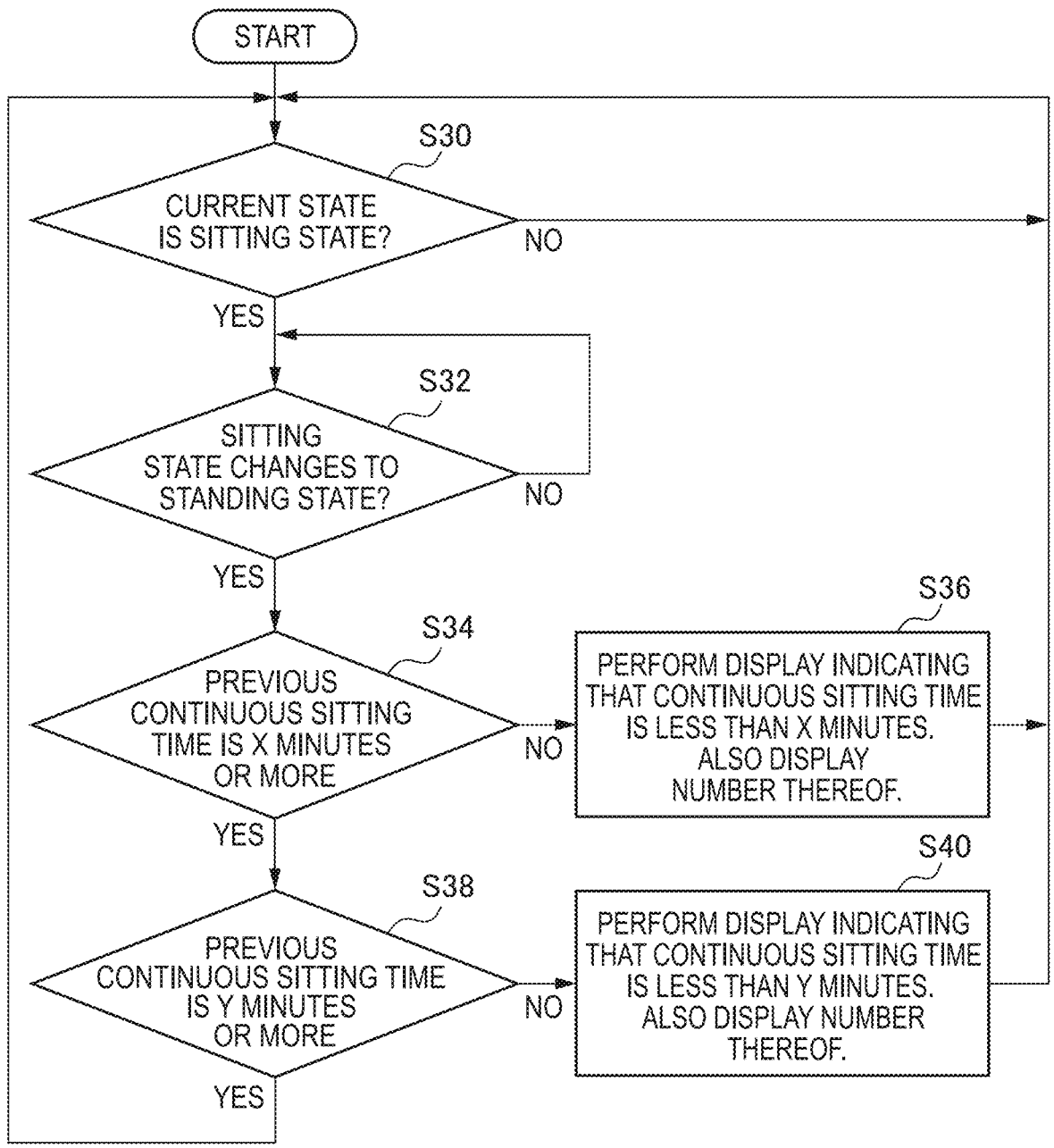
FIG. 7 is a flowchart describing the processing for displaying the display indicating that the continuous sitting time is less than X minutes and the display indicating that the continuous sitting time is less than Y minutes.

FIG. 7 is a flowchart describing processing for displaying the display 208 indicating that the continuous sitting time is less than X minutes and the display 210 indicating that the continuous sitting time is less than Y minutes. First, in a step S30, it is determined whether or not the current state is the sitting state and, if the current state is the sitting state, the flow proceeds to a step S32. On the other hand, if the current state is not the sitting state, the flow waits at the step S30. In the step S32, it is determined whether or not the sitting state changes to the standing state and, if the sitting state changes to the standing state, the flow proceeds to a step S34. On the other hand, if the sitting state does not change to the standing state in the step S32, the flow waits at the step S32.

In the step S34, it is determined whether or not the previous continuous sitting time is X minutes or more. As an example, X is set as 30. Then, if the previous continuous sitting time is less than X minutes in the step S34, the flow proceeds to a step S36. In the step S36, the display 208 indicating that the previous continuous sitting time is less than X minutes is displayed at the time when it is determined that the sitting state changes to the standing state in the step S32. Further, the number of the displays 208 described in FIG. 4 is also displayed. After the step S36, the flow returns to the step S30.

Further, if the previous continuous sitting time is X minutes or more in the step S34, the flow proceeds to a step S38. In the step S38, it is determined whether or not the previous continuous sitting time is Y minutes or more. As an example, Y is set as 60. Then, if the previous continuous sitting time is less than Y minutes in the step S38, the flow proceeds to a step S40. In the step S40, the display 210 indicating that the previous continuous sitting time is less than Y minutes is displayed at the time when it is determined that the sitting state changes to the standing state in the step S32. After the step S40, the flow returns to the step S30. Further, if the previous continuous sitting time is Y minutes or more in the step S38, the flow returns to the step S30. Note that, as described above, the continuous sitting time is recognized by the recognition portion 124 of the control portion 120. The recognition portion 124 recognizes a result obtained by comparing the time during which the sitting state continues and one or more threshold values (X minutes and Y minutes).

When the display 208 indicating that the continuous sitting time is less than X minutes and the display 210 indicating that the continuous sitting time is less than Y minutes are displayed as shown in FIG. 6 in a manner described above, the user can confirm the frequency of the changes from the sitting state to the standing state and the continuous sitting time by visually recognizing the displays 208 and 210. This allows the user to recognize that the low frequency of the changes from the sitting state to the standing state affects the user's health, thereby motivating the user to change the sitting state to the standing state. As a result, the user can avoid the health risk. Further, the user can confirm the continuous sitting time by visually recognizing the displays 208 and 210, allowing the user to recognize that the relatively long continuous sitting time affects the user's health, thereby motivating the user to shorten the continuous sitting time. As a result, the user can avoid the health risk.

When the aforementioned displays 206, 208, and 210 are displayed, a sound may be simultaneously generated. In this case, the sound control portion 126 generates the sounds corresponding to the displays 206, 208, and 210. This allows the user to surely recognize the contents of the displays 206, 208, and 210 by the sounds. Further when the displays 206, 208, and 210 are displayed, a message such as "The continuous standing time is too long. Please stand up" may be displayed together.

5. Cooperation with Other Devices Such as Smartphone and Server

Figure 8:
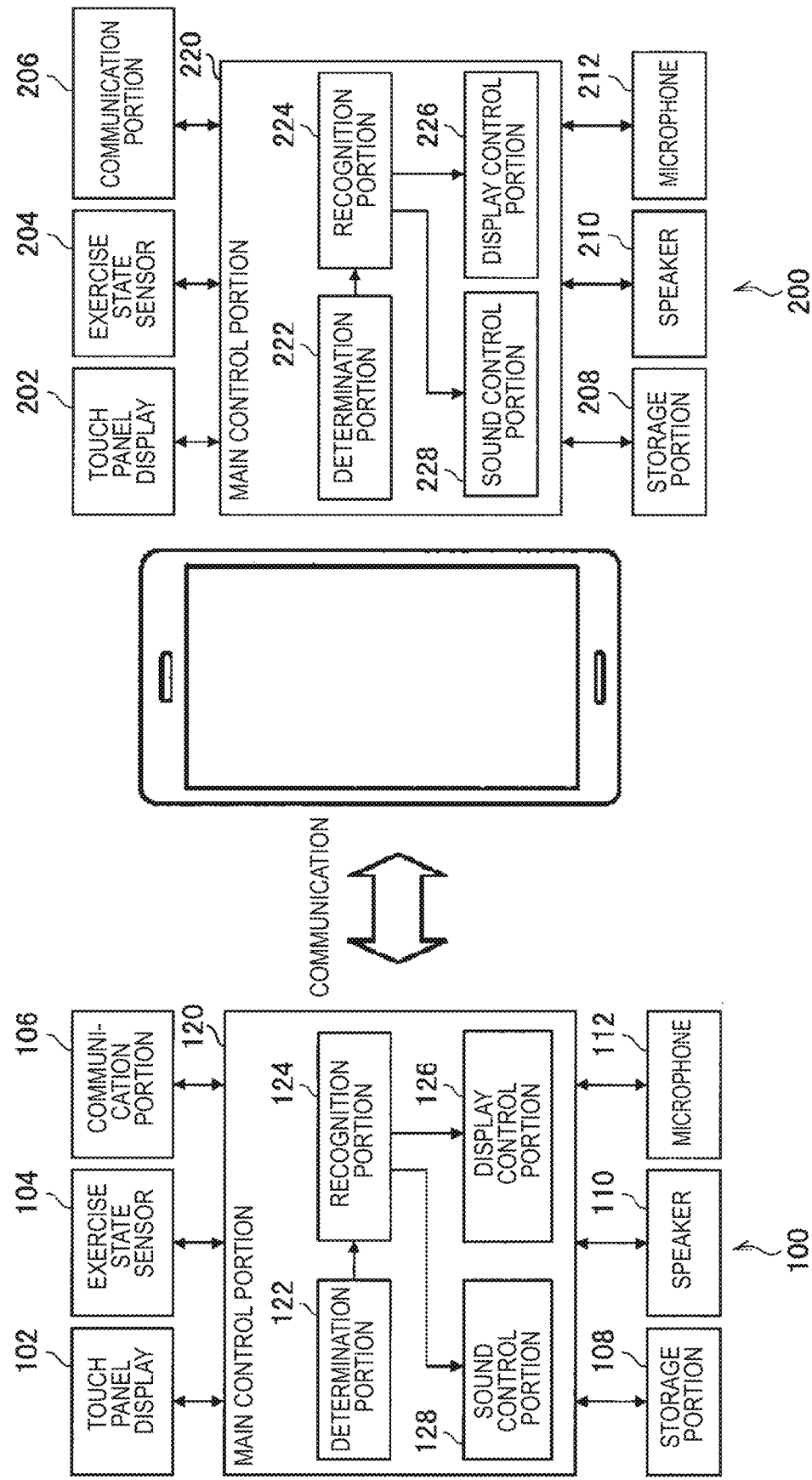
FIG. 8 is a schematic diagram illustrating a configuration example in which a wearable device such as a wrist watch type device and a head mounted display (HMD) and a smartphone perform radio communication.

In the example described above, the device 100 put on the body of the user is configured to perform all processing. However, the configuration of the control portion 120 of the device 100 may be included in other devices. FIG. 8 shows a configuration example in which a wearable device such as a wrist watch type device and a head mounted display (HMD) is used as the device 100 and the device 100 and a smartphone 200 perform radio communication. As shown in FIG. 8, the smartphone 200 includes a control portion 220 configured similarly to the control portion 120 of the device 100. Further, similar to the device 100, the smartphone 200 is configured by including a touch panel display 202, an exercise state sensor 204, a communication portion 206, a storage portion 208, a speaker 210, and a microphone 212. Detection values of the heart rate and the acceleration detected by the exercise state sensor 104 of the device 100 are sent from the communication portion 106 to the communication portion 206. The control portion 220 of the smartphone 200 performs processing similar to that of the control portion 120. The touch panel display 202 of the smartphone 202 performs display similar to that shown in FIG. 4 and FIG. 6. Further, a processing result of the main control portion 220 can be sent from the communication portion 206 to the communication portion 106 to perform the display shown in FIG. 4 and FIG. 6 on the touch panel display 102 of the device 100.

The determination portion 122 and the recognition portion 124 of the control portion 120 and the determination portion 222 and the recognition portion 224 of the control portion 220 in FIG. 8, respectively, have similar functions, thus the processing of the determination portions 122 and 224 and the processing of the recognition portions 124 and 224 may be each performed by the cooperation of both portions. Further, in a case where the processing is performed only by the determination portion 222 and the recognition portion 224 of the control portion 220 of the smartphone 200, the determination portion 122 and the recognition portion 124 of the main control portion 120 may be omitted.

Figure 9:
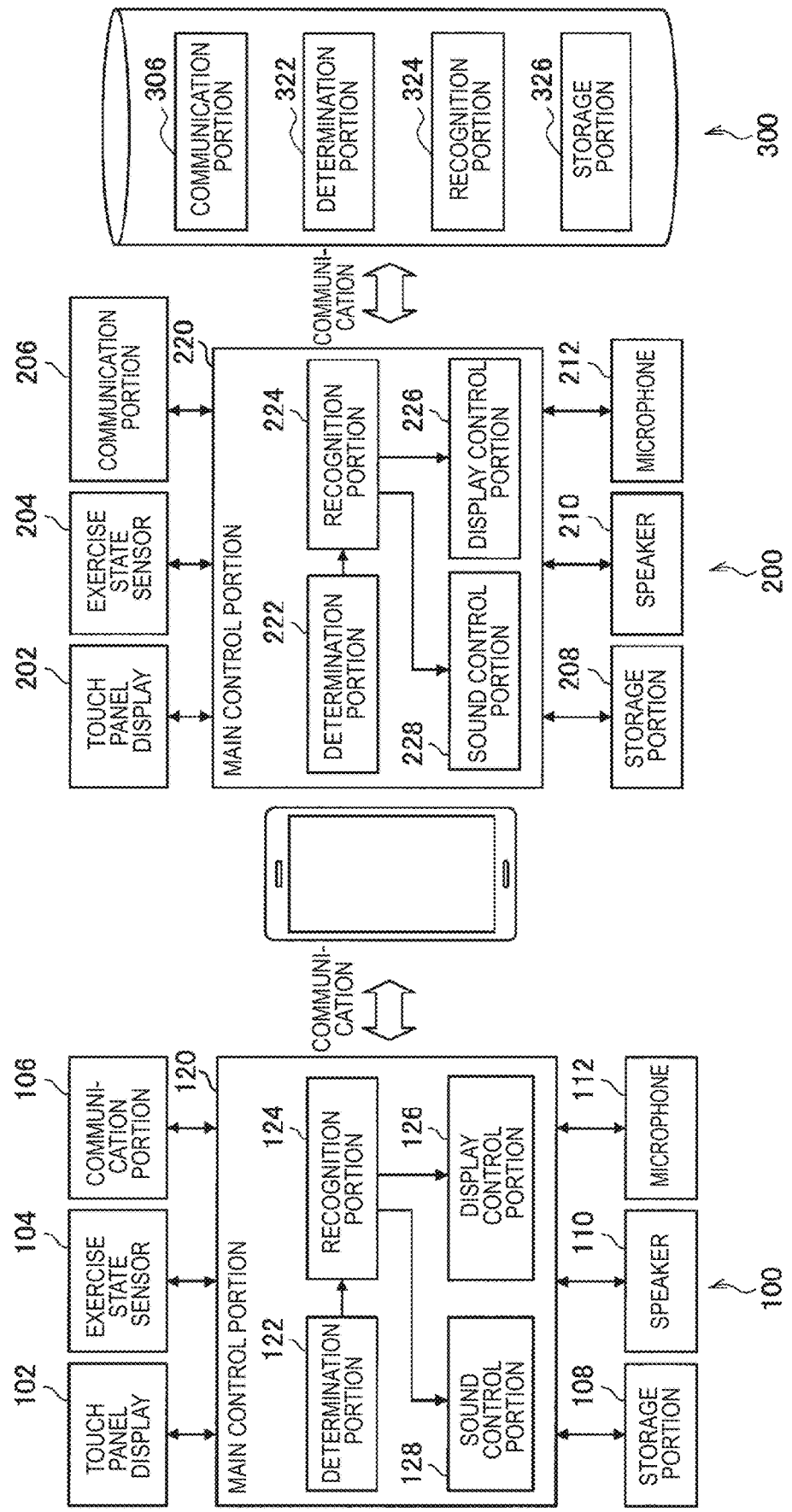
FIG. 9 is a schematic diagram illustrating an example in which the smartphone, in addition to having the configuration in FIG. 8, communicates with a server.

Further, FIG. 9 is a schematic diagram illustrating an example in which the smartphone 200, in addition to having the configuration in FIG. 8, communicates with a server 300. The server 300 may be provided, for example, on a cloud. As shown in FIG. 9, the server 300 includes a determination portion 322 and a recognition portion 324 configured similarly to the determination portion 122 and the recognition portion 124 included in the control portion 120 of the device 100. Further, the server 300 includes a communication portion 306 that performs communication with the smartphone 200 and a storage portion 326 that stores various data. The detection values of the heart rate and the acceleration detected by the exercise state sensor 104 of the device 100 are sent from the communication portion 106 to the communication portion 206 of the smartphone 200. Further, the detection values of the heart rate and the acceleration detected by the exercise state sensor 104 of the device 100 are sent from the communication portion 206 of the smartphone 200 to the communication portion 306 of the server 300. The determination portion 322 and the recognition portion 324 of the server 300 perform processing similar to that of the determination portion 122 and the recognition portion 124 included in the control portion 120 of the device 100. Processing results of the determination portion 322 and the recognition portion 324 of the server 300 are sent from the communication portion 306 to the communication portion 206 to performs display similar to that shown in FIG. 4 and FIG. 6 on the touch panel display 202 of the smartphone 200. Further, the processing results of determination portion 322 and the recognition portion 324 of the server 300 can be sent from the communication portion 206 of the smartphone 200 to the communication portion 106 of the device 100 to perform the display shown in FIG. 4 and FIG. 6 on the touch panel display 102 of the device 100.

Note that each constituting element of the control portion 100 of the device 100, the smartphone 200, and the server 300 can be constitute by a hardware, or a central processing unit such as CPU and a program (a software) for causing the central processing unit to perform the function. Further, the communication portion 106, the communication portion 206, and the communication portion 306 perform wireless or wired communication without a particular limitation in their communication systems.

Also in FIG. 9, the determination portion 122 and recognition portion 124 of the control portion 120, the determination portion 222 and the recognition portion 224 of the control portion 220, and the determination portion 322 and the recognition portion 324 of the server 300, respectively, have similar functions, thus the processing of the determination portions 122, 222, and 322 and the processing of the recognition portions 124, 224, and 324 may be each performed by the cooperation of these portions. Further, in a case where the processing is performed only by the determination portion 322 and the recognition portion 324 of the server 300, the determination portion 122 and the recognition portion 124 of the main control portion 120 and the determination portion 222 and the recognition portion 224 of the main control portion 220 may be omitted.

As described above, according to the present embodiment, the display 206 indicating the time when the sitting state changes to the standing state, the display 208 indicating that the continuous sitting time is less than X minutes, and the display 210 indicating that the continuous sitting time is less than Y minutes are configured to display. In this manner, the user can confirm the frequency of the changes from the sitting state to the standing state and the continuous sitting time by visually recognizing the displays 206, 208 and 210. This allows the user to recognize that the low frequency of the changes from the sitting state to the standing state affects the user's health, thereby motivating the user to change the sitting state to the standing state. As a result, the user can avoid the health risk. Further, the user can confirm the continuous sitting time by visually recognizing the displays 208 and 210, allowing the user to recognize that the relatively long continuous sitting time affects the user's health, thereby motivating the user to shorten the continuous sitting time. As a result, the user can avoid the health risk.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device including:

a determination portion that determines, on the basis of information regarding an exercise state of a user, whether the exercise state of the user is a sitting state or a standing state; and a display processing portion that performs processing for displaying at least one of a time when the exercise state of the user changes from the sitting state to the standing state or the number of times the exercise state of the user changes from the sitting state to the standing state.

(2)

The information processing device according to (1), in which the determination portion determines the standing state, on the basis of the information, if a motion amount of the user is the motion amount equivalent to walking or less and more than the motion amount equivalent to sitting.

(3)

The information processing device according to (1) or (2), in which the display processing portion performs the processing for displaying the number of times the sitting state of the user changes to the standing state within a predetermined time.

(4)

The information processing device according to any one of (1) to (3), in which the determination portion determines, on the basis of the information, that the exercise state of the user is an active state if the exercise state of the user is more than a motion amount equivalent to walking, and the display processing portion displays which one of the sitting state, the standing state, and the active state the user is in.

(5)

The information processing device according to any one of (1) to (4), including a recognition portion that recognizes a time during which the sitting state continues if the exercise state of the user changes from the sitting state to the standing state, in which the display processing portion performs the processing for displaying the time during which the sitting state continues.

(6)

The information processing device according to (5), in which the recognition portion recognizes a comparison result obtained by comparing the time during which the sitting state continues and one or more threshold values, and the display processing portion performs the processing for displaying the comparison result.

(7)

The information processing device according to any one of (1) to (6), further including a sound control portion that performs processing for outputting, via sound, at least one of the time when the exercise state of the user changes from the sitting state to the standing state or the number of times the exercise state of the user changes from the sitting state to the standing state.

(8)

A program for causing a computer to function as:

a means of determining, on the basis of information regarding an exercise state of a user, whether the exercise state of the user is a sitting state or a standing state; and a means of performing processing for displaying at least one of a time when the exercise state of the user changes from the sitting state to the standing state or the number of times the exercise state of the user changes from the sitting state to the standing state.

REFERENCE SIGNS LIST

100 device
122, 222, 322 determination portions
124, 224, 324 recognition portions
126, 226 display control portions

The invention claimed is:

1. An information processing device, comprising:
 a determination portion configured to:
  determine whether an exercise state of a user is one of a sitting state or a standing state, based on information associated with the exercise state of the user;
  determine a number of times the exercise state of the user changes from the sitting state to the standing state, in a specific time period;
 a recognition portion configured to:
  determine a continuous sitting time of the user for which the exercise state is in the sitting state, based on the changes in the exercise state from the sitting state to standing state; and
  determine whether the continuous sitting time is less than at least one threshold value; and
 a display processing portion configured to:
  display a number of times the continuous sitting time is less than at least one threshold value within the specific time period; and
  display at least one of:
   a time at which the exercise state changes from the sitting state to the standing state, or
   the number of times the exercise state changes from the sitting state to the standing state, in the specific time period.

2. The information processing device according to claim 1, wherein
 the determination portion is further configured to determine that the exercise state is the standing state, based on information associated with a motion amount of the user, and
 the exercise state is determined as the standing state, in a case where:
  the motion amount of the user is less than or equal to a first motion amount associated with walking, and
  the motion amount of the user, is greater than or equal to a second motion amount associated with sitting.

3. The information processing device according to claim 1, wherein
 the determination portion is further configured to determine that the exercise state of the user is an active state, based on the information associated with the exercise state of the user,
 the exercise state is determined as the active state, in a case where a motion amount of the user is more than a motion amount associated with walking, and
 the display processing portion is further configured to display the exercise state of the user.

4. The information processing device according to claim 1, wherein the display processing portion is further configured to display the continuous sitting time.

5. The information processing device according to claim 1, further comprising:
 a sound control portion configured to output sound corresponding to at least one of:
  the time at which the exercise state changes from the sitting state to the standing state, or
  the number of times the exercise state changes from the sitting state to the standing state in the specific time period.

6. A non-transitory computer-readable medium, having stored thereon, computer-executable instructions that, when executed by a computer, cause the computer to execute operations, the operations comprising:
 determining whether an exercise state of a user is one of a sitting state or a standing state, based on information associated with the exercise state of the user;
 determining a number of times the exercise state of the user changes from the sitting state to the standing state, in a specific time period;

determining a continuous sitting time of the user for which the exercise state is in the sitting state, based on the changes in the exercise state from the sitting state to standing state;

determining whether the continuous sitting time is less than at least one threshold value;

displaying a number of times the continuous sitting time is less than at least one threshold value within the specific time period; and displaying at least one of:
- a time at which the exercise state changes from the sitting state to the standing state, or
- the number of times the exercise state changes from the sitting state to the standing state, in the specific time period.

* * * * *